(12) United States Patent
Bergenudd et al.

(10) Patent No.: US 8,800,829 B2
(45) Date of Patent: Aug. 12, 2014

(54) STRESS-REDUCER FOR SHOULDER AND THE USE THEREOF

(75) Inventors: Hampus Bergenudd, Bjaerred (SE); Per Ekdahl, Lund (SE)

(73) Assignee: All of it Scandinavia AB, Bjärred (SE)

( * ) Notice: Subject to any disclaimer, the term of this patent is extended or adjusted under 35 U.S.C. 154(b) by 453 days.

(21) Appl. No.: 12/096,116

(22) PCT Filed: Nov. 27, 2006

(86) PCT No.: PCT/SE2006/001344
§ 371 (c)(1),
(2), (4) Date: Jun. 4, 2008

(87) PCT Pub. No.: WO2007/067124
PCT Pub. Date: Jun. 14, 2007

(65) Prior Publication Data
US 2008/0283562 A1    Nov. 20, 2008

Related U.S. Application Data

(60) Provisional application No. 60/789,621, filed on Apr. 5, 2006.

(30) Foreign Application Priority Data

Dec. 5, 2005  (SE) ..................................... 0502677

(51) Int. Cl.
*A45F 3/12*   (2006.01)

(52) U.S. Cl.
USPC ............ 224/264; 224/201; 224/265; 224/266

(58) Field of Classification Search
USPC ......... 224/188, 201, 247, 264, 265, 266, 270, 224/272, 600, 905, 907, 925; 396/420; 84/280; 2/459
See application file for complete search history.

(56) References Cited

U.S. PATENT DOCUMENTS

| 2,370,611 | A | * | 2/1945 | Du Mais | 294/139 |
| 2,633,573 | A | * | 4/1953 | Sanders | 2/460 |
| 2,746,336 | A | * | 5/1956 | Bisharat | 84/280 |

(Continued)

FOREIGN PATENT DOCUMENTS

| GB | 2153211 A2 | 8/1985 |
| WO | 0167901 A1 | 5/1983 |
| WO | 2008002617 A1 | 1/2008 |

*Primary Examiner* — Adam Waggenspack
(74) *Attorney, Agent, or Firm* — Birch, Stewart, Kolasch & Birch, LLP

(57) ABSTRACT

A stress-reducer is provided for reducing stress on a user from a load of a carried item or object. The stress-reducer is shaped as a yoke and worn over a shoulder of a user and supports the carried item or object. The yoke bridges or spans the shoulder of the user, substantially the upper part of the trapezius muscle and/or the collarbone. The yoke is in contact with either side of the upper part of the user's shoulder on an anterior and/or posterior side. The stress-reducer can be used with strap means. A carried item, equipped with a stress-reducer, a brassiere fitted with a stress-reducer and a garment having a stress-reducer attached thereto are also provided, as well as an arm carrier comprising a stress-reducer, a cradle being attached to an arm and a string being connected between the stress-reducer and the cradle.

7 Claims, 6 Drawing Sheets

(56) References Cited

U.S. PATENT DOCUMENTS

| | | | | |
|---|---|---|---|---|
| 3,504,377 A | * | 4/1970 | Biggs, Jr. et al. | 2/462 |
| 3,547,322 A | * | 12/1970 | Dawson et al. | 224/148.2 |
| 3,682,358 A | * | 8/1972 | Richey | 224/201 |
| 3,767,095 A | * | 10/1973 | Jones | 224/261 |
| 4,091,975 A | * | 5/1978 | Russell, Jr. | 224/265 |
| 4,139,132 A | | 2/1979 | Fairchild, Jr. | |
| 4,280,645 A | | 7/1981 | Goodden | |
| 4,304,167 A | | 12/1981 | Tait | |
| 4,507,801 A | * | 4/1985 | Kavanagh et al. | 2/462 |
| 4,564,008 A | * | 1/1986 | Donahoo | 602/4 |
| 4,799,610 A | * | 1/1989 | Hsieh | 224/266 |
| 4,858,801 A | | 8/1989 | Sameniego | |
| 4,874,120 A | | 10/1989 | Paton et al. | |
| 5,215,239 A | | 6/1993 | Walters, Jr. | |
| 5,361,956 A | * | 11/1994 | Recanati | 224/257 |
| 5,431,320 A | | 7/1995 | Hash | |
| 5,590,826 A | | 1/1997 | Endo | |
| 5,973,247 A | | 10/1999 | Matthews | |
| 5,975,984 A | | 11/1999 | Tart | |
| 6,040,509 A | | 3/2000 | Fanella | |
| 6,250,525 B1 | | 6/2001 | Lehoux | |
| 6,257,633 B1 | | 7/2001 | Katz | |
| 6,467,661 B1 | * | 10/2002 | Mistretta et al. | 224/264 |
| 6,481,022 B1 | | 11/2002 | D'Addario et al. | |
| 6,581,812 B2 | | 6/2003 | Roscoe-Dare | |
| 6,640,344 B2 | | 11/2003 | D'Addario et al. | |
| 6,683,237 B2 | | 1/2004 | Christou | |
| 6,698,633 B2 | * | 3/2004 | Finkelstein | 224/264 |
| 2002/0100109 A1 | | 8/2002 | Hoop | |
| 2003/0046750 A1 | | 3/2003 | D'Addario et al. | |
| 2004/0060951 A1 | | 4/2004 | Kelly | |
| 2004/0256426 A1 | | 12/2004 | Sanderson et al. | |
| 2005/0020184 A1 | | 1/2005 | Izcoa | |
| 2005/0173481 A1 | * | 8/2005 | La Greca | 224/264 |
| 2005/0183565 A1 | | 8/2005 | May | |
| 2007/0039983 A1 | * | 2/2007 | Harrison et al. | 224/265 |

* cited by examiner

STRESS-REDUCER FOR SHOULDER AND THE USE THEREOF

CROSS-REFERENCE TO RELATED APPLICATION

This application is the U.S. national phase of PCT Application Serial No. PCT/SE2006/001344 filed Nov. 27, 2006 which claims priority to Sweden Application Serial No. 0502677-8 filed Dec. 5, 2005 and claims the benefit of U.S. Provisional Application Ser. No. 60/789,621 filed Apr. 5, 2006.

FIELD OF THE INVENTION

The present invention relates to a device for reducing stress on a user from a load of a carried item or object. It further relates to a carried item being equipped with a device of the invention. It moreover relates to a garment being equipped with such a device, and an arm carrier for carrying the weight of a user's arm, as well as a use of a device according to the invention.

BACKGROUND OF THE INVENTION

Shoulder straps are fitted on many items in order to make it easier to carry them. Such items are e.g. musical instruments, backpacks, golf bags, child carriers, laptop computer cases, attaché cases, handbags etc. Shoulder straps are also fitted on brassieres and in this case carry the weight of a woman's breasts. Traditional shoulder straps transfer a stress to a user's shoulder and neck area, e.g. the trapezius muscle. Prolonged exposure to a heavy weight via a shoulder strap often leads to pain and fatigue and can eventually lead to headache, injury and neck problem.

One way of reducing this problem is to equip the shoulder strap with a cushioning pad of a soft material. Such a pad distributes the weight from the strap over a larger area, thus reducing the pressure, but the downward force on the upper part of the shoulder area is not reduced.

A typical example of a shoulder pad for a guitar strap is disclosed in U.S. Pat. No. 6,481,022 to D'Addorio et al. This pad is configured to better distribute the weight of a carried item, such as a guitar, over a larger area. However, the weight is still supported by the upper part of the shoulder. Other devices, such as shoulder harnesses, are designed to shift some of the load to straps or belts that encircle the chest or the waist, but this will lead to restricted breathing and/or chafing of the hip and waist area.

Carry golf bags are today often equipped with two shoulder straps, and the bag is carried as a backpack. The use of two shoulder straps balances the weight evenly on the body and also distributes the downwardly directed force to two straps. The straps are equipped with cushioning material for reducing the contact pressure, but the weight is taken up by the upper part of the trapezius muscle and collarbone.

Laptop computer cases are today often equipped with one shoulder strap, and the bag is carried on one shoulder with the shoulder strap either diagonally over the body or straight on one side of the body. The strap is typically equipped with cushioning material for reducing the contact pressure, but the weight is also here taken up by the upper part of the trapezius muscle and the collarbone.

SUMMARY OF THE INVENTION

In order to mitigate, alleviate or eliminate at least partly one or several of the above-mentioned problems, it is an object of the present invention to provide a stress-reducer for reducing the stress in the shoulder area, for example on the upper part of the shoulder, such as the trapezium muscle and/or the collarbone, of a user when carrying an item e.g. by a shoulder strap.

In one aspect of the invention, there is provided a device for reducing stress on a user's body from a load and for being worn over a shoulder of the body for supporting said load, comprising a yoke for bridging or spanning a shoulder area of the body and for transferring said load onto either side of the shoulder area, such that stress on the shoulder area is avoided during use.

In an embodiment, the device may comprise a base portion for bridging or spanning said shoulder area; and two end portions for abutting said body below said shoulder area for supporting said weight. The yoke may be in contact with the body at an area below said shoulder area on an anterior side, such as the pectoral muscle, and at an area on a posterior side, such as the lower part of the trapezius muscle or Latissimus dorsi.

In an embodiment, at least one end portion of the yoke, being in contact with the body, may be more flexible than a base portion of the yoke.

In an embodiment, the device may further comprise a strap member. The rigidity of the yoke may be achieved in combination with the strap member attached thereto. The yoke may be connected to a strap member at both end portions, whereby the yoke forms a part of the strap member. The end portions may comprise strap members integral with the end portions.

In an embodiment, the yoke may comprise pads of a soft material at least one end portion.

In an embodiment, the device may comprise a hook or loop for maintaining the strap member on the yoke. A hook-and-loop fastener may be arranged that interacts with a corresponding fastener on the strap member.

In an embodiment, a plate may be provided that interconnects two yokes. The plate may comprise a member for attaching said weight.

In an embodiment, the device may comprise upwardly protruding sidewalls, extending at least partially from one end portion to the other end portion, forming a channel for maintaining the strap member therein.

In an embodiment, the device may comprise two limbs interconnected by a fastener for forming said yoke. The fastener may comprise an elongated hole in a first limb and a hole in the other limb, and a connecting member arranged in said holes for securing the limbs together.

In an embodiment, the device may comprise two limbs joined with a hinge at its substantially central part, close to the apex of the yoke.

In an embodiment, the two limbs may be joined at their centrally located ends, close to the apex of the yoke, by a pivot permitting rotation of the limbs about an axis perpendicular to the surfaces of the centrally located ends, which axis is substantially vertical when the yoke is used. The two limbs may be joined by a hinge at its substantially central part, close to the apex of the yoke, making it pivotable outwardly and inwardly, and that one of the limbs comprises a protrusion that restricts relative outward rotation of the limbs.

In an embodiment, the yoke may be adapted to maintain the base portion of the yoke at a predetermined distance above the upper part of the shoulder in use.

In an embodiment, at least one of the end portions may be wider than the base portion. Moreover, the base portion may be wider than at least one of the end portions.

In another aspect, there is provided a carried item, such as a guitar, a bass, an accordion, drums, a backpack, a golf bag, a handbag, a duffel bag, an attaché case, a laptop computer case, a weapon, machinery for forestry, gardening, a user-carried machinery, comprising the above-mentioned device.

In a further aspect, there is provided a brassiere comprising the above-mentioned device.

In a still further aspect, there is provided a garment, comprising at least one of the above-mentioned devices, said device being attached to the garment bridging an upper part of the user's shoulder, when the garment is used.

In an embodiment, the device may be fixedly attached to or integral with the garment. The device may be removably arranged inside a pocket of the garment.

In a yet further aspect, there is provided an arm carrier, comprising the above-mentioned device, and further comprising a cradle for attachment to an arm, said cradle having a strap or string that is connected between the cradle and the device, such that the weight of the arm is transferred to the device.

In an embodiment, the string may be a sling, worn by a person having an arm injury. The cradle may be a plaster cast for an arm, said cast comprising fastening means, such as a hook or loop.

In a yet another aspect, there is provided a harness for hunters, military personal, police officers, photographers, forest or garden workers, comprising the above-mentioned device. The harness may comprise at least two devices.

BRIEF DESCRIPTION OF THE DRAWINGS

Further objects, features and advantages of the invention will become apparent from the following detailed description of several embodiments of the invention with reference to the drawings, in which.

DETAILED DESCRIPTION OF EMBODIMENTS

Below several embodiments of the invention are described in detail in order to enable a skilled person to carry out the invention and for disclosing the best mode. However, such embodiments do not limit the invention, but other combinations of the different features are possible within the scope of the invention.

A stress-reducer 1 is intended to be used for reducing stress that can occur when heavy items or objects are carried by, or the load thereof is transferred to, a user's body, e.g. by means of a shoulder band or strap. The stress-reducer can make up the shoulder strap or form a part of a strap. Consequently, the term "strap member" is used as a general description of a strap 2 or a stress-reducer 1 serving as or being a part of a strap.

Different examples of stress-reducers will be given below with references to the appended drawings. References will be made to positions shown on the drawings or relative to a potential user, such as upper, lower, right, left, but this is only for illustrative purposes and is not intended to limit the scope of the invention.

Figure 1:
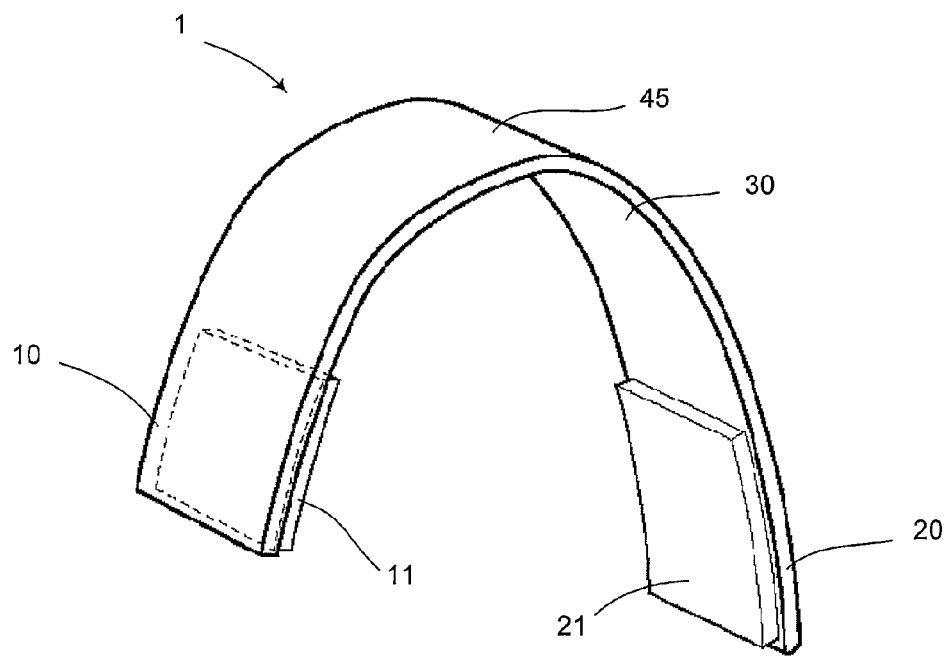
FIG. 1 is a perspective view of a stress-reducer.

An embodiment of a stress-reducer 1 can be formed as a yoke with an inverted U-shape, see FIG. 1. The yoke can be manufactured from a single material, such as plastic, wood, metal. The yoke can comprise a laminate comprising glass fiber, carbon fiber or Kevlar® together with a resin. The yoke can also be made from combinations of the above-mentioned materials.

Figure 2:
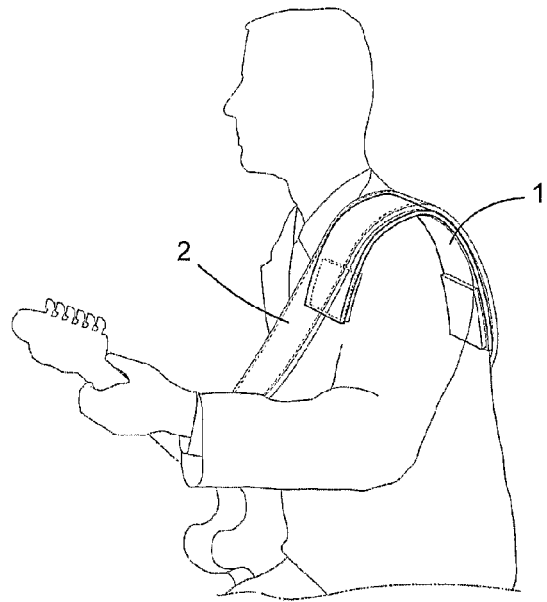
FIG. 2 is a perspective view a user carrying a guitar with a stress-reducer.

The stress-reducer 1 can be used in connection with a strap 2 of a carried item, such as a guitar as is shown in FIG. 2.

The stress-reducer has a front or anterior end portion 10 and a rear or posterior end portion 20, being connected by a load-bearing base portion 30. The stress-reducer is used as shown in FIG. 2 with the yoke arranged on top of the shoulder with the end portions 10 and 20 being supported by a body portion below the shoulder region. The stress-reducer is so arranged that the base portion 30 is not in contact with the upper part of the shoulder, but the stress-reducer is entirely supported by the contact between the end portions 10 and 20 and the body.

The base portion 30 should be sufficiently rigid so that it does not flex down into contact with the upper part of the shoulder when it is subjected to or supports a moderately heavy carried item. The front 10 and rear 20 end portions may be provided with pads 11, 21 or similar of a soft material, such as plastic foam or rubber. The end portions 10, 20 can also be made more resilient than the load-bearing base 30 so that the end portions 10, 20 themselves distribute the contact pressure on the users body over a larger area or over an angle.

Figures 3A, 3B:
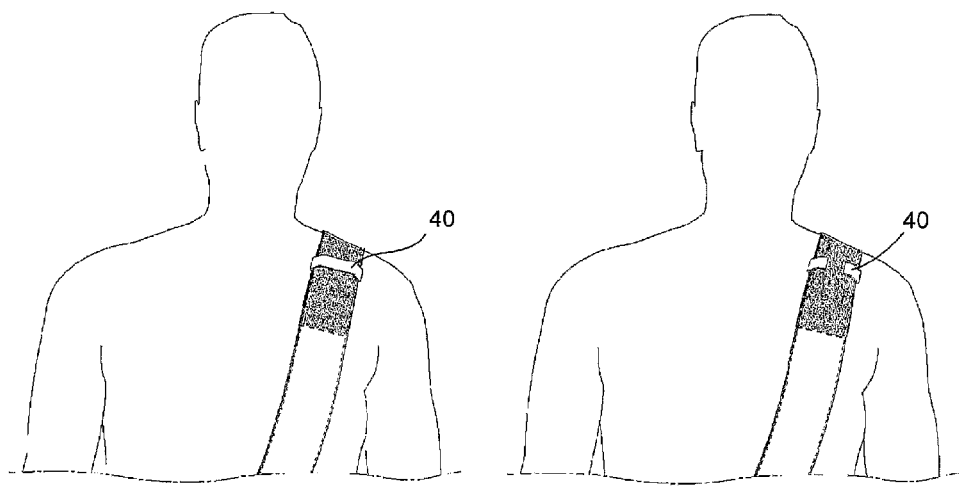
FIGS. 3a and 3b are frontal views of a user with different embodiments of the stress-reducer.

The stress-reducer 1 can be formed with hooks or loops 40 for inserting a strap 2 of an item to be carried, such as a guitar, a backpack, a golf bag, a handbag, a duffel bag, an attaché case or similar, e.g. see FIGS. 3a and 3b. These hooks or loops 40 can also secure the strap 2 to the stress-reducer, so that the stress-reducer and/or the strap cannot slide off during use.

Figures 4A, 4B:
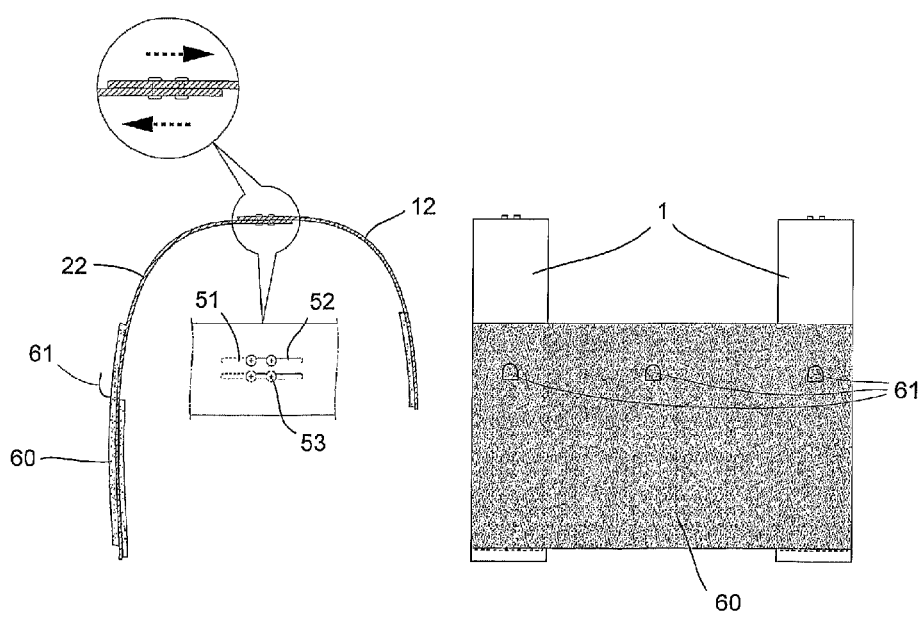
FIGS. 4a and 4b are a side-view and a back-view, respectively, of an assembly of two stress-reducers and a back plate, where the stress-reducers are adjustable.

FIGS. 4a and 4b disclose a second embodiment of the stress-reducer 1, where two elongated limbs 12, 22 are joined to form an inverted U-shape. At least one of the limbs 12, 22 is provided with an elongated hole or slit 51 and the other limb 22, 12 is provided with a hole or slit 52, which also may be elongated as shown in the Figure, and the two limbs 12, 22 are clamped together by several screws and nuts 53 or similar, see FIG. 4a. This makes it possible to regulate the size of the stress-reducer 1 in order to adjust it to shoulders of different sizes. The screws 53 are loosened and the two limbs 12, 22 of the stress-reducer can be pulled apart or pushed together, depending on the requested size of the stress-reducer 1. The screws 53 are then tightened and the stress-reducer 1 is ready to be used. The nuts may also be integrated in one of the limbs 12, 22. Instead of screws and nuts, other members performing substantially the same action can be used, such as snap fasteners, cam locking surfaces, nuts and bolts, locking wedges etc.

This makes the stress-reducer adjustable so that one size can be used for many different users. The stress-reducer typically only needs to be adjusted the first time, and will then have correct size for the specific user. This adjustability can also be used to adapt to thick clothes, if the stress-reducer is worn on the outside of the clothes.

Figures 5A, 5B:
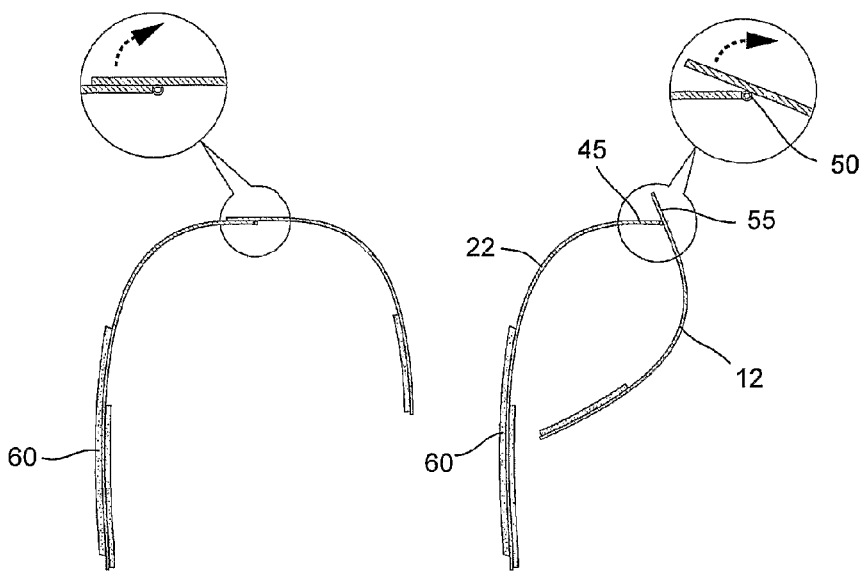
FIGS. 5a and 5b are side-views of an alternative, collapsible embodiment of the stress-reducer.

One embodiment of the stress-reducer 1 can be articulated by using a pivot 50 e.g. being arranged at an apex or terminal 45 of the stress-reducer 1, see FIGS. 5*a* and 5*b*. One of the limbs 12, 22 can then be formed with a protrusion 55 that restricts further pivoting at a certain position, the operating position. This will make the stress-reducer 1 foldable, which is advantageous for some applications.

The stress-reducer 1 can alternatively be formed with a pivot 50 and can have clamping means (not shown) arranged for clamping the strap 2 on an underside of the stress-reducer 1. The strap 2 should be sufficiently rigid in the longitudinal direction for this embodiment to work. When the stress-reducer 1 is rotated outwardly, the length of the inner periphery will increase. Hence, the length of the strap 2 inside the stress-reducer 1 will determine the end position. This will also enable folding of the stress-reducer 1 while still maintaining a bridging or spanning ability at an operation position. By loosening the clamps about the strap 2, its length along the periphery of the stress-reducer can be chosen and this will make the stress-reducer 1 adjustable to users of different sizes. This is only possible if the pivot is at some distance above the contact area of the strap, so that outward flexing leads to a longer inner periphery of the stress-reducer.

Figures 6A, 6B:
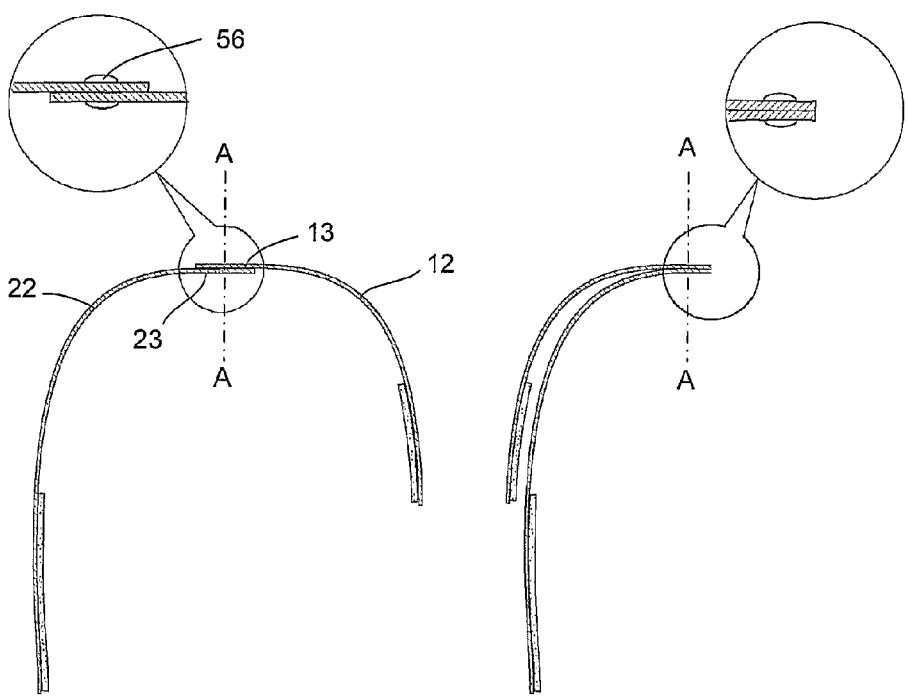
FIG. 6 is another alternative of a collapsible embodiment of the stress-reducer.

FIGS. 6*a* and 6*b* disclose still another collapsible embodiment of the stress-reducer. This embodiment is equipped with a hinge or pivot 56 that allows relative rotation of the two limbs 12, 22 about a substantially vertical axis A-A. A centrally located end 13 of one the two limbs 12 will then substantially fit on top of a centrally located end 23 of the other limb 22. The limbs 12, 22 can be rotated relative to one another so that one limb 12 is located on top of the other limb 22, and this will make the stress-reducer 1 very compact. Which limb 12, 22 that goes over the other are unimportant. This embodiment may be equipped with a holding means (not shown), for fixing the stress-reducer at a certain position, e.g. an operating position (FIG. 6*a*) and a folded position (FIG. 6*b*).

Another embodiment can be equipped with means for fastening a strap member at either end of the device (not shown). In this case, the stress-reducer 1 will form a part of the strap 2. The fastening means can either be formed in the strap, such as a hole, hook and loop fastener, a snap connector or similar, or in the stress-reducer 1, such as a knob for the hole in the strap, a slit for entering a strap having hook and loop fastener or clamping means of a general nature.

The stress-reducer 1 can also be formed with a channel on an upper side, wherein a strap 2 can be placed. The stress-reducer 1 can then even be fitted underneath a garment and will not be visible to a potential audience. The channel may be formed by providing generally vertical walls on opposite longitudinal sides of the stress-reducer 1. The walls extend upwards and the channel is formed there-between.

In all embodiments, separate fixing means can be arranged for keeping the stress-reducer in place on the body, such as a strap 25 around the chest.

The stress-reducer 1 can also be integrated into a strap 2, so that the end portions 10, 20 of the stress-reducer 1 are prolonged and are flexible enough to be used as straps. The stress-reducer 1 should still be provided with contact surfaces that transfer the weight of the carried item to the body at opposite sides of the shoulder.

FIGS. 4*a* and 4*b* shows that two stress-reducers 1 can be connected to a substantially rigid plate 60 and form a carrying structure. The plate can be adapted for attaching various items or bags, and will be operational without any strap 2. The structure can simply be placed on top of the shoulders, and the weight of an item, attached to the plate 60, will be transferred to a front and rear area of the user's body. The plate 60 may be arranged on the front area or back area of the stress-reducer. The plate 60 may comprise hooks 61, loops, hook-and-loop fasteners, as seen in FIGS. 4*a* and 4*b* for attaching an item to be carried.

The stress-reducer 1 can also be fitted in or used with a shoulder strap of a brassiere. This will greatly reduce the discomfort from the shoulder strap cutting into the upper part of the shoulder area. The stress-reducer 1 may then be made smaller, but must still bridge or span the upper part of the shoulder. The contacting end portions 10, can either be formed at the end of the strap 2, or be integrated in an upper part of the cup of the brassiere. The stress-reducer 1 can also in this case be provided with a hinge, if desired.

The stress-reducer 1 can be coupled with or connected to the strap 2 by either using the hooks or loops 40 or by placing the strap 2 in the channel. As mentioned, hook-and-loop fastener (such as Velcro®) can be used to secure the strap 2 to the stress-reducer 1.

An assembly of two stress-reducers 1 and a back plate 60 can be used for carrying different kinds of items. Bags or items are then fastened to the back plate 60, and the assembly can be used with or without a strap 2. The assembly can also be formed with a linking element between the front ends 10, 12 of the stress-reducers, see for example FIG. 10.

Figure 8:
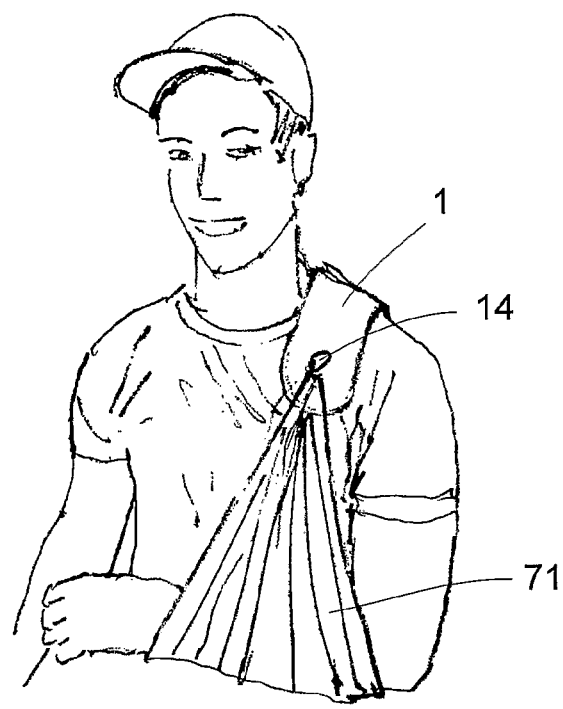
FIG. 8 illustrates a boy having a sling that is attached to a stress-reducer.

In one embodiment, the stress-reducer 1 is equipped with a hook on the front and/or back end portions 10, 20. For a person with an arm injury or with his/her arm in cast, this hook can be used for attaching a sling for carrying the arm. In this way, the traditional sling around a wearer's neck can be removed, with resulting reduced stress on the wearer. The sling is fastened in a hook 14 on the stress-reducer, see FIG. 8, and is attached to the arm via e.g. an armband, a hook in the cast, a cradle 72 below the arm or is simply wrapped around the arm, see for example FIG. 10.

Figure 10:
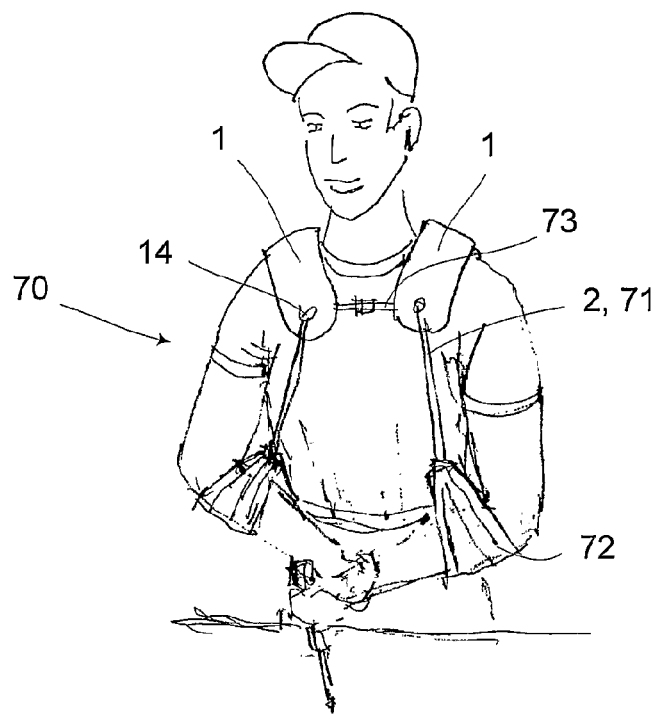
FIG. 10 illustrates an arm carrier comprising two stress-reducers.

One embodiment of the stress-reducer can be used by people working in an assembly line. These workers are often subjected to monotonous working conditions, which require them to lift their arms for long time periods. By wearing two stress-reducers, one on each shoulder, the weight of the wearer's arms can be carried by the stress-reducers by attaching a string 2, 71 to e.g. a cradle 72, an arm band or similar, as can be seen in FIG. 10. The string is then attached to a hook 14 on the stress-reducer. This resembles the function of top-mounted or ceiling-mounted arm carriers, which today are found at some factories with assembly lines. The arm carrier 70 of this embodiment, however, is much more flexible and allows the wearer to move more freely from one task to another or from one station to another. It is possible to use only one stress-reducer, if only one arm needs relief. If two stress-reducers 1 are used, they can be interconnected with a central strap 73.

The shape of the stress-reducer is to some extent determined by and can be adapted to its intended use. The load-bearing base 30 should be sufficiently rigid to withstand the load from the carried item, without collapsing and contacting the upper part of the shoulder, and transfer the load to the contacting end portions 10, 20. The base 30 can be relatively wide, to accommodate a strap of a carried item, or be narrow if nothing is to be placed on top of the stress-reducer. The end portions 10, should have a sufficiently large size to support and distribute the contact force from the carried item or object. The contact areas may each be in the range of 15 to 150 $cm^2$, depending on the application. A larger contact area can distribute a heavier load from the stress-reducer.

Figures 9A, 9B:
FIGS. 9a and 9b illustrates two different shapes of an end portion of the stress-reducer.

The end portions 10, 20 can have a shape as seen in FIG. 9a, with an increase width of the contact area. This makes it possible to shorten the front end portion 10, making it suitable for female wearers since the end portion 10 will transfer load onto an area above a top portion of her breast. The shape in FIG. 9b is also possible, when the stress is moderate and a relatively small contact area can be used, or for male users where the stress-reducer can make contact further down on the breast area.

Figure 11:
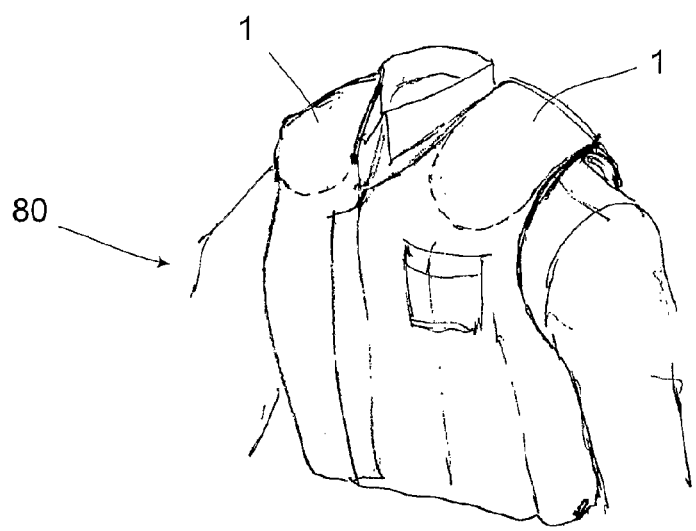
FIG. 11 illustrates a garment being equipped with two stress-reducers.

In one embodiment, one or two stress-reducers 1 can be arranged in a garment 80, such as a vest for building workers, see FIG. 11. This will protect the workers when they lift a heavy item on their shoulder. In one embodiment, a wider load-bearing base 30 is provided, so that items can be carried directly on the shoulder without contacting the underlying muscles. The stress-reducer can be sewn into the garment or can be arranged in closable pockets in the shoulder portion of the garment. One or two stress-reducers can be provided in the garment, depending on the requirement or desire of the user. A stress-reducer having a wider base 30 can also be used on the outside of a garment, for carrying sacks and similar on the shoulder.

The material of the stress-reducer 1 should be sufficiently stiff to withstand the weight or load from the carried or supported item or object. Various kinds of plastic materials are possible, such as PA 6, a mix of polyamide and nylon, aromatic polyamide of the Grivory type and tailored materials with different fillers, e.g. LNP materials from GE Plastics, at One Plastics Ave., Pittsfield, Mass. 01201. The above polyamide materials can be mixed with fillers such as glass fiber. A fiber content of about 25-50% is possible, and PA 6 with a fiber content of about 30% is suitable. The Grivory type polyamide may be mixed with 50% glass fiber. The filler reinforces the plastic and increases its stiffness. The LNP materials can be made with high-strength properties and can be used for more demanding applications, where heavy loads can be supported or where the dimensions of the stress-reducer must be reduced.

The stress-reducer 1 can have different designs depending on the specific application. The design can in some embodiments be provided with one or several stiffening ribs, especially if the overall design or shape of the stress-reducer is relatively weak. Alternatively, the stress-reducer is made to incorporate stiffening features in the overall design.

The shape of the load bearing base 30 can be slightly curved or angled, as seen from the front end portion 10 to the back end portion 20. This angle can be most clearly seen from above, and the load-bearing base will then have a shape that curves or angles around the neck, albeit at some distance, which can be used for increasing the distance between the base of the stress-reducer and the neck. This can give increased protection of the neck. The angle can easily be adjusted if the stress-reducer is manufactured as two separate pieces that are assembled into a unit, e.g. in the manner as is seen in FIGS. 6a and 6b.

The end portions 10, 20 of the stress-reducer may in some embodiments be provided with pads 11, 21 that make contact with the body. These pads distribute the pressure from the load and/or provide good friction between the stress-reducer and the wearer or his/her clothes. Suitable materials are silicon or thermoplastic elastomer (TPE), which can be molded or cast into a suitable shape, or some form of cellular plastic or expanded plastic, where pads can be punched from a flat sheet. It is also possible to use thermoforming of the cellular plastic, and the shape can then be more freely chosen. The pads can optionally be provided with a textile fabric or similar on the surface facing the wearer. If the pads are molded or cast, the pads can be made solid in order to increase the wear-resistance.

The stress-reducer 1 is intended for being used with a shoulder strap 2 when carrying relatively heavy items. It can also be used for carrying lighter items for a longer time period. The strap 2 with the stress-reducer 1 is placed over a shoulder of the user and the stress-reducer should then be placed so that it does not contact a shoulder area but contacts an area of the body below the shoulder area, e.g. an area adjacent the pectoral muscle in the front-side and an area adjacent a Latissimus dorsi muscle in the back-side. The weight of the carried item will now be transferred to the stress-reducer and then to at least one of the contact areas of the body and will then typically be routed to the spine and to the legs. Substantially no weight or load will be taken up by the upper area of the shoulder, since the base 30 transfers the load to the end portions 10, 20. Thus, the upper part of the trapezius muscle and/or the collarbone is left unaffected. In some situations, load on the trapezius muscle at the upper part of the shoulder should be avoided and in some situations, load should be avoided on the collarbone. Normally, load is avoided on both of these regions when a stress-reducer 1 is worn and it is used for its rated load.

A sensitive region in the upper part of the shoulder is the upper part of the trapezius muscle, where a lot of nerves are located that run from the spine to the side of the body. If this area is loaded, the nerves can be subjected to stress, and this may lead to pain in the neck and shoulder region. Too much stress, either brief or prolonged, can lead to injury and incapacitation.

Figure 7:
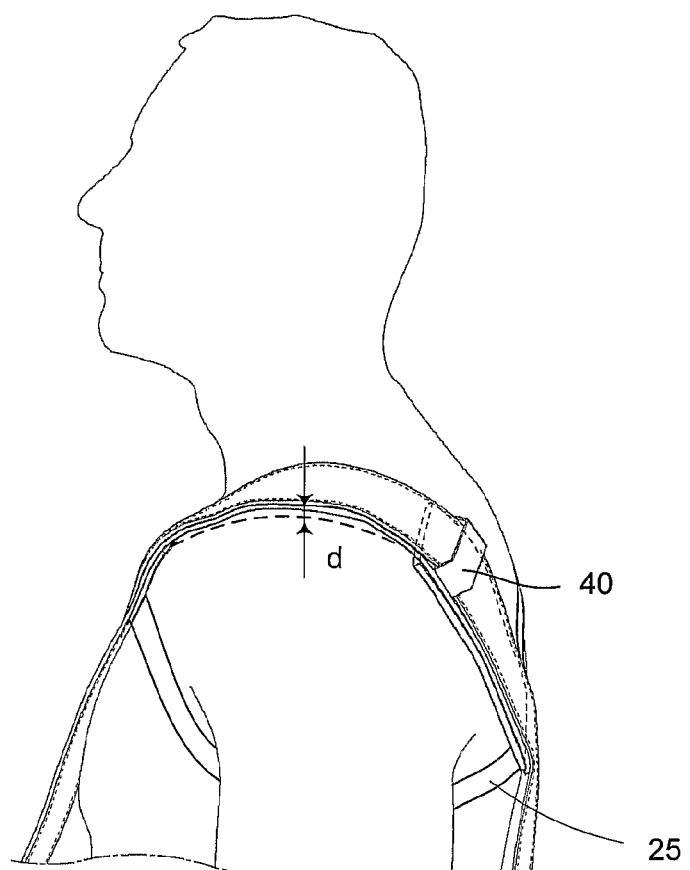
FIG. 7 is a side-view of a user wearing a stress-reducer equipped with a loop for a strap.

The stress-reducer 1 will extend over the trapezius muscle and maybe also the collarbone, and form a gap therebetween. This is shown as a distance d in FIG. 7, wherein the upper part of the shoulder is given by the dashed line. The distance d indicates that there is no load on the upper part of the shoulder, but the actual size of the distance is of less importance. The load will then be zero on the upper part of the trapezius muscle and/or the collarbone.

In the above embodiments, the load-bearing base 30 does not comprise a pad or a resilient material, since the base should not be in contact with the upper part of the shoulder during use. Thus, in the above embodiments solely the end portions are provided with pads. The underside of the base 30 is thus bare, and is not intended for being in contact with a user's body. This reduces the overall cost of the stress-reducer, since only a small amount of pad material is necessary. The end portions 10, 20 do not have to comprise pad material, but a pad can make the end portion softer and more adjustable to the contour of the user's body. This can help prevent points with high contact pressure.

In an alternative embodiment, it is possible to use a bridging or spanning device, which is arranged for merely reducing the contact pressure on said upper shoulder area. The bridging device can then be used in combination with a pad that contacts the upper part of the trapezius muscle.

If the stress-reducer is worn over a garment or an article of clothing, the cloth of the garment should be loose below the stress-reducer or be drawn up against the load-bearing base 30. Otherwise, the stress-reducer might drag the cloth downwardly on both sides of the wearer. This is caused by a slight downward sliding movement that can occur between the stress-reducer and the body, which is caused by outward flexing of the stress-reducer when it is loaded. The dragging will create a tension in the cloth, which can then transfer a load onto the upper part of the shoulder. This is not a large problem, since it as mentioned above is easily remedied. If the cloth of the garment is flexible, this will be an even smaller problem.

During use, the weight may be transferred from a carried item via a strap to the upper part of the stress-reducer 1. Load can also be transferred to the stress-reducer in other ways, such as via a hook 14 being located somewhere on the stress-reducer 1, see e.g. FIG. 8. If the hook 14 is located close to or in an end portion 10, 20, the load will be unevenly distributed on the two end portions 10, 20. This is no problem, as long as the stress-reducer safely remains in its location, where it bridges the upper part of the shoulder.

The stress-reducer 1 can be used with many different items that are carried or be used for supporting a weight, such as a guitar, an accordion, drums, a backpack, a carry golf bag, a handbag, a child carrier, a duffel bag, an attaché case, laptop computer cases, or similar. It can also be used in a harness or strap for carrying a clearing saw, a turbo-trimmer or vibrators for concrete work. It can further be used with harnesses for guns or harnesses for lifting heavy items generally. Other professionals, e.g. hunters, military personal, police officers, photographers, forest or garden workers etc, may also use such harnesses that are suitable for being provided with a stress-reducer 1 according to some of the above embodiments.

The stress-reducer 1 does not require a strap in order to work, and can just as well be coupled to an item to be carried by any other connecting means, such as bars, links, or similar constructions.

The stress-reducer 1 having a substantially inverted U-shape, such as a yoke, comprises a load-bearing base 30, and has a front 10 and a rear 20 end portion at either end thereof, said stress-reducer being adapted to be worn over a shoulder and only transferring a load, received by the load-bearing base 30, via the end portions 10, 20 to an anterior and posterior side of a user, when in use. Said load-bearing base should be sufficiently stiff to bridge or span over the upper part of the user's shoulder, when being used up to its rated load.

Although the invention has been described with reference to specific forms and embodiments, it will be evident for a person skilled in the art that alterations and modifications can be made without departing from the scope of the invention. The different features may be combined in different manners than explicitly shown in the drawings. The invention is only limited by the appended claims.

The invention claimed is:

1. A device for being worn over a shoulder of a user's body for supporting a load, the device comprising:
    a generally U-shaped base portion spanning a trapezius muscle of the user's body, wherein the base portion is maintained at a predetermined distance above the trapezius muscle so that the device does not contact the trapezius muscle;
    an anterior portion extending from the base portion and comprising a pad for abutting a the user's body at the anterior side of the shoulder below the trapezius muscle; and
    a posterior end portion extending from the base portion and comprising a pad for abutting the user's body at the posterior side of the shoulder below the trapezius muscle,
    wherein the anterior and posterior end portions transfer the load via the pads onto the anterior and posterior sides of the user's body below the trapezius muscle so that only the pads of the device contact the user's body in order to reduce stress on the trapezius muscle of the user's body from supporting the load;
    wherein the pad of the anterior end portion is positioned at a first distance from an upper apex point of the base portion, which first distance is larger than a distance from an upper point of the user's shoulder to a collarbone of the user, whereby in use the pad of the anterior end portion is arranged below the collarbone and the base portion is maintained at a predetermined distance above the collarbone; and
    wherein the pad of the posterior end portion is positioned at a second distance from the upper apex point of the base portion, which second distance is larger than the first distance.

2. The device according to claim 1, wherein the posterior portion is longer than the anterior portion.

3. A device for being worn over a shoulder of a user's body for supporting a static load, the device comprising:
    a yoke for transferring the load onto both sides of a shoulder top area, such that stress on and contact with the shoulder top area is avoided during use, the yoke comprising:
        a base portion bridging the shoulder top area; and
        an anterior end portion extending from the base portion and comprising a pad for abutting an anterior side of the user's body; and
        a posterior end portion extending from the base portion and comprising a pad for abutting a posterior side of the user's body; and
    a strap member, one end of which is connected to said static load for supporting said static load and the other end of which is connected to a fastening means arranged at said anterior end portion so as to be adjacent to said anterior end portion at an end thereof opposite from the base portion,
    wherein the base portion of the yoke is maintained at a predetermined distance above said shoulder top area so that said shoulder top area is free from contact with said device in order to reduce stress on the user's body from said static load and the device abutting the user's body only via said pads; wherein the pad of the anterior end is positioned at a first distance from an upper apex point of the base portion, which first distance is larger than a distance from an upper point of the user's shoulder to a collarbone of the user, whereby in use the pad of the anterior end portion is arranged below the collarbone and the base portion is maintained at a predetermined distance above the collarbone; and wherein the pad of the posterior end portion is positioned at a second distance from the upper apex point of the base portion, which second distance is larger than the first distance.

4. The device according to claim 3, wherein at least one end portion is more flexible than the base portion of the yoke.

5. The device according to claim 3, wherein the anterior end portion abuts the user's body below the shoulder top area at a pectoral muscle, and the posterior end portion abuts the user's body below the shoulder top area at a latissimus dorsi muscle, wherein said posterior end portion is longer than said anterior end portion.

6. The device according to claim 3, wherein the pad of the posterior end portion of the yoke is in contact with the user's body below the shoulder top area at a latissimus dorsi muscle.

7. The device according to claim 3, wherein the pad of the anterior end portion is in contact with the user's body below the shoulder top area at a pectoral muscle.

* * * * *